（12) United States Patent
Lei (10) Patent No.: US 9,867,526 B2
(45) Date of Patent: Jan. 16, 2018

(54) ENDOSCOPE WITH ADJUSTABLE VIEWING ANGLE (75) Inventor: Fang Lei, Durchhausen (DE)

(73) Assignee: Karl Storz SE & Co. KG, Tuttlingen (DE)

(*) Notice: Subject to any disclaimer, the term of this patent is extended or adjusted under 35 U.S.C. 154(b) by 6 days.

(21) Appl. No.: 13/560,495

(22) Filed: Jul. 27, 2012

(65) Prior Publication Data
US 2013/0030251 A1 Jan. 31, 2013

(30) Foreign Application Priority Data

Jul. 28, 2011 (DE) ........................ 10 2011 079 958

(51) Int. Cl.
A61B 1/06 (2006.01)
A61B 1/07 (2006.01)
A61B 1/00 (2006.01)
G02B 3/14 (2006.01)
G02B 23/24 (2006.01)

(52) U.S. Cl.
CPC .............. *A61B 1/07* (2013.01); *A61B 1/0019* (2013.01); *A61B 1/00183* (2013.01); *A61B 1/0615* (2013.01); *A61B 1/0623* (2013.01); *G02B 3/14* (2013.01); *G02B 23/2423* (2013.01)

(58) Field of Classification Search
CPC ......... A61B 1/07; A61B 1/043; A61B 1/0638; A61B 1/0684; A61B 1/00174; A61B 1/00181; A61B 1/00183; A61B 1/00188
USPC ........ 600/160, 173, 178, 179, 180, 163, 177
See application file for complete search history.

(56) References Cited

U.S. PATENT DOCUMENTS

| 6,261,226 B1 | 7/2001 | McKenna et al. |
| 7,126,903 B2* | 10/2006 | Feenstra et al. ......... 369/112.23 |
| 2007/0112256 A1* | 5/2007 | Terakawa et al. ............ 600/178 |
| 2008/0021279 A1* | 1/2008 | Takahashi .......... A61B 1/00091 600/151 |
| 2009/0021818 A1 | 1/2009 | Weir et al. |
| 2009/0043156 A1 | 2/2009 | Igarashi et al. |
| 2009/0177033 A1 | 7/2009 | Hendriks et al. |
| 2009/0252485 A1* | 10/2009 | Tsuchiya ....................... 396/200 |
| 2010/0010301 A1* | 1/2010 | Hale et al. .................... 600/109 |
| 2010/0282954 A1* | 11/2010 | Hendriks et al. .......... 250/227.2 |
| 2011/0118610 A1* | 5/2011 | Kuiper et al. ................ 600/476 |
| 2011/0201889 A1* | 8/2011 | Vayser ............... A61B 1/00135 600/182 |
| 2012/0063142 A1* | 3/2012 | Cameron et al. ............. 362/277 |

(Continued)

FOREIGN PATENT DOCUMENTS

DE 60015375 T2 2/2006
DE 102009049143 B3 * 12/2010 ......... A61B 1/00066

(Continued)

OTHER PUBLICATIONS

German Search Report; Application No. DE 10 2011 079 958.3; dated May 8, 2012; 5 pages.

*Primary Examiner* — Alexandra Newton
(74) *Attorney, Agent, or Firm* — Whitmyer IP Group LLC (57) ABSTRACT An endoscope includes a light outlet surface at the distal end of the endoscope and a controllable light-refracting device for controllable refraction of illuminating light by a shapeable phase interface between two fluids, such that the controllable light-refracting device is disposed at the distal end of the endoscope.

11 Claims, 3 Drawing Sheets (56) References Cited

U.S. PATENT DOCUMENTS

2012/0136213 A1* 5/2012 Weimer ............ A61B 1/00066
600/173

FOREIGN PATENT DOCUMENTS

| WO | 2004051323 A1 | 6/2004 |
| WO | 2007033326 A2 | 3/2007 |

* cited by examiner

ENDOSCOPE WITH ADJUSTABLE VIEWING ANGLE

CROSS-REFERENCE TO RELATED APPLICATIONS

The present application claims priority of German patent application No. 10 2011 079 958.3 filed on Jul. 28, 2011, the content of which is incorporated herein by reference.

FIELD OF THE INVENTION

The present invention relates to an endoscope with an adjustable viewing angle.

BACKGROUND OF THE INVENTION

In addition to endoscopes for medical and non-medical technical applications, whose viewing angle is parallel to the longitudinal axis of the endoscope shaft, endoscopes with other fixed viewing angles have been developed for some time. The viewing angle of an endoscope is understood here and hereinafter always to mean the direction facing from the distal end of the endoscope, in which an object is situated that appears in the center of the image recorded by means of the endoscope. In many applications, however, a fixed viewing angle is a disadvantage. In the worst case, for example during a medical procedure, the endoscope must be replaced numerous times. In such cases it is an advantage to use an endoscope with a viewing angle that can be selected or adjusted in situ.

Observing an object in a cavity by means of an endoscope assumes as a rule that there is some illumination of the object. For this purpose an endoscope comprises, for example, lightwave conductors, in particular glass fibers, by means of which an illuminating light is transmitted from the proximal end of the endoscope along the shaft to the distal end of the endoscope. Light outlet surfaces of the lightwave conductors on the distal end of the endoscope are positioned and configured in such a way that the entire visual field or viewing field is sufficiently and homogeneously illuminated.

In an endoscope with adjustable viewing angle, the illuminating light on the distal end of the endoscope, in the simplest case, is distributed in such a way that the entire visual field is illuminated independently of the particular viewing angle selected. This results, however, in a series of disadvantages. In particular, light capacity is wasted, because the entire visual fields of all selectable viewing angles are illuminated constantly, independently of the viewing angle that is actually selected. Thus, at a predetermined desired brightness, a markedly higher lighting capacity must be provided altogether than with an endoscope with a fixed viewing angle.

An additional disadvantage arises from the fact that illuminating light of high intensity can photo-thermally or photo-chemically damage tissue or other objects. With an endoscope with fixed viewing angle, the distal end of the endoscope is at too close a distance to an object, at least on observing the recorded image. In using a video camera on the endoscope, an automatic warning of users is also possible if the brightness of a recorded image exceeds a predetermined threshold. With an endoscope with adjustable viewing angle, however, part of the illuminating light impinges on objects lying outside the visual field. Therefore there is no undesired approach of the distal end of the endoscope to these objects, and no resulting illumination of these objects with too high a radiant capacity.

A further disadvantage consists in the fact that illuminating light radiated outside the visual field can also be dispersed or reflected by objects or opaque media. The reflected or dispersed illuminating light can arrive directly or indirectly in the observation beam path. Consequently, contrasts and the distinguishability of objects, especially in dark image areas, can be reduced.

An additional disadvantage comes from the fact that the illuminating intensity or intensity of the illuminating light is essentially constant in the direction in which the viewing angle can be varied (often referred to also as the vertical direction), while it decreases slightly as a rule toward the edge of the visual field in the direction perpendicular thereto (often also called the horizontal direction). However, users of endoscopes with fixed viewing angle are as a rule accustomed to an illuminating intensity that slightly declines toward the edge of the visual field both in the horizontal and in the vertical directions. The illuminating intensity that is constant in the vertical direction can therefore be experienced as an irritant.

Patent application DE 600 15 375 T2 describes an arrangement of several prisms. One of the prisms can be rotated around an axis in order to cast illuminating light at an adjustable viewing angle. The prisms, however, require a structural space that is not available in every endoscope. In addition, it can become burdensome in practice, with the arrangements described in DE 600 15 375 T2, to achieve simultaneously a strong degree of optical isolation of the illuminating and observation beam paths, considerable light strength in the observation beam path, low losses in the illuminating beam path and a small shaft diameter.

SUMMARY OF THE INVENTION

An object of the present invention consists in providing an improved endoscope with adjustable viewing angle.

This object is achieved through the contents of the independent claims.

Refinements are indicated in the dependent claims.

An endoscope includes a light outlet surface on the distal end of the endoscope and a controllable light-refracting device for controllable refraction of illuminating light by means of a shapeable phase interface between two fluids, such that the controllable light-refracting device is positioned on the distal end of the endoscope.

The endoscope is, in particular, an endoscope for medical or technical applications, also known in the latter case as a boroscope. The light-refracting device includes, in particular, in a hermetically sealed-off hollow space, two liquids or a liquid and a gas, which are not mixable or are only mixable in a limited quantity and therefore constitute a defined phase interface with a positive interface tension or interface energy. For example, the light-refracting device includes water or a salt solution or other hydrophilic or lipophobic liquid and an oil or other lipophilic or hydrophobic liquid.

The two fluids are, in particular, transparent for the intended illuminating light and comprise various refractive indices. Because of the different refractive indices, illuminating light is refracted at the phase interface between the two fluids in accordance with the Snellius law of refraction. Refraction of the illuminating light depends on the form or shape of the phase interface, in particular on the direction of the surface normals and on the curvature of the phase interfaces.

The light-refracting device can be configured in order to tip the phase interface in essentially flat shape around one or more axes. This means that at a given moment all surface normals of the phase interface are equal or essentially equal and can be pivoted together around one or two axes. Alternatively or in addition, the curvature of the phase interface can be modified. In particular, the phase interface comprises at every moment primarily, extensively or completely a positive Gaussian curvature $K=k_1 \times k_2$, such that the two main curvatures $k_1$, $k_2$ can be modified simultaneously or synchronously or independently of one another.

The controllable light-refracting device, in particular, is positioned on the distal end of the endoscope directly upstream in the light path from the light outlet surface. The controllable light-refracting device is thus disposed, in particular, directly below or bordering on the outer surface of the endoscope.

The controllable light-refracting device on the distal end of the endoscope makes it possible to divert illuminating light at an adjustable angle and/or in a solid angle or area of adjustable size and shape. The controllable light-refracting device on the distal end of the endoscope allows an adjustment of the illumination to an adjustable viewing angle and/or to an adjustable focal length of an object lens in the observation beam path of the endoscope. This makes it possible to avoid a few of the aforementioned disadvantages of an illumination independent of an adjustable viewing angle and/or of an adjustable size of the visual field.

In particular, the light capacity falling on objects outside the momentary visual field, and thus the photo-thermal or photo-chemical damage to said objects, can be reduced. In addition the reflection or scattering of illuminating light to non-observed objects can be reduced and thus image quality can be improved. Moreover, the distribution of illuminating light can be adjusted to the visual habits of the users, who as a rule are accustomed to a maximum illuminating strength or intensity in the image center and to an illuminating strength or intensity that declines proceeding from the center toward all sides. In addition, with a given illuminating light source, objects inside the momentary visual field can be illuminated more brightly or, at equally bright illumination of the momentary visual field, a weaker illuminating light source can be selected.

Embodiments described hereinafter make possible, in addition, an extensive miniaturization of the light-refracting device. The use of the controllable light-refracting device on the distal end of the endoscope therefore poses no obstacle to increasing miniaturization of endoscopes.

In an endoscope as described here, the light outlet surface on the distal end of the endoscope is a light outlet surface of the controllable light-refracting device.

If the light outlet surface of the controllable light-refracting device is simultaneously the light outlet surface of the endoscope at its distal end, reflections on other interfaces can be avoided and the required structural space can be further reduced.

An endoscope as described here can comprise a number of light outlet surfaces on the distal end, such that one light-refracting device is disposed at each of the number of light outlet surfaces.

Each light-refracting device is, in particular, disposed immediately upstream in the light path from the associated light outlet surface, such that the associated light outlet surface of the endoscope can be identical in each case with the light outlet surface of the light-refracting device. A plurality of light outlet surfaces allows, for example, an illumination of objects free of shadows or low in shadows if the light outlet surfaces are disposed at opposite sides of a light inlet surface in an observation beam path. In addition, a plurality of light outlet surfaces with a plurality of light-refracting devices can allow an enlargement of the area that can be illuminated or a concentration of the available light on a given area.

In addition to the plurality of light outlet surfaces, with which one light-refracting device is associated in each case, the endoscope can comprise one or more additional light outlet surfaces without associated light-refracting device.

In an endoscope as described here, the controllable light-refracting device is configured in particular at least either for adjusting the illuminating direction or for adjusting the opening angle of the area that is to be illuminated.

In an endoscope as described here, the light-refracting device can comprise a cross-section, of which at least either the surface or the width increases in the foreseen propagation path of illuminating light.

Alternatively, in an endoscope as described here, the light-refracting device can comprise a cross-section of which at least either the surface or the width decreases in the foreseen propagation path of illuminating light.

The cross-section is understood to mean a cross-section perpendicular or essentially perpendicular to the foreseen light path direction or center light path direction inside the light-refracting device. The light path direction or center light path direction is, in particular, the direction from a light inlet surface to a light outlet surface of the light-refracting device. Because of a cross-section of the light-refracting device that varies in the foreseen light path direction, the divergence of illuminating light can be modified. For example, because of a cross-section that grows narrower in the light path direction, the divergence of illuminating light can be increased or, owing to a cross-section that becomes wider in the light path direction, the divergence of illuminating light can be reduced. Thus, the light-refracting device can contribute toward adapting the distribution of illuminating light to the size of the area that is to be illuminated.

In addition, an endoscope as described here can comprise a field-generating device to generate an electrical or magnetic field to form the phase interface.

Possible field-generating devices can include, in particular, electrodes to generate an electro-static field or electrical alternating field, or one or more coils to generate a static or time-dependent magnetic field. An electric field generated by a field-generating device influences the shape or form of the phase interfaces, in particular when the two fluids comprise different permittivities or dielectricity numbers. A magnetic field generated by the field-generating device influences the form of the phase interface in particular when the two fluids comprise different magnetic susceptibilities or different magnetic permeabilities. Coils and especially electrodes can be extensively miniaturized, so that they accept a small structural space and allow miniaturization of the light-refracting device and endoscope.

An endoscope as described here, in which at least either the viewing angle or the visual field angle is adjustable, includes in particular a control device to generate a control signal to control the light-refracting device, such that the control device is configured in order at least to control the light-refracting device either depending on the adjusted viewing angle or depending on the adjusted visual field angle.

The control signal is, in particular, an electrical tension signal that can be applied directly to electrodes of the light-refracting device, or an electrical current signal that can be applied directly to a coil of the light-refracting device.

The endoscope and the control device of the endoscope are, in particular, configured in such a way that users can adjust the viewing angle at a user interface of the endoscope, such that the control device independently controls the light-refracting device in such a way that illuminating light is diverted in a direction corresponding to the viewing angle. Alternatively or in addition, the endoscope and the control device are configured in such a way that users, at the user interface of the endoscope, can adjust the visual field angle or the solid angle within which simultaneously recorded objects are situated, such that the control device independently controls the light-refracting device in such a way that the solid angle area in which illuminating light is radiated corresponds to the visual field angle. This can make possible a simple and efficient operation or use of the endoscope.

In an endoscope as described here, with a control device, the latter can be configured to generate one control signal for several light-refracting devices.

In particular, the control device is coupled by several signal lines with one of a number of light-refracting devices in each case, in order to control the light-refracting devices independently of one another and thus to allow a still better adjustment of the illuminating area to the observed area.

An endoscope as described here can, in addition, include a light conductor to transmit illuminating light to the distal end of the endoscope with a light outlet surface, which is disposed at the distal end of the endoscope, such that the light-refracting device is disposed between the light outlet surface of the light conductor and the light outlet surface of the endoscope.

The light conductor is configured in particular to transmit illuminating light from the proximal end of the endoscope to the distal end of the endoscope. A light source can be provided at the proximal end of the endoscope. Alternatively, the proximal end of the endoscope can be coupled via a light conductor cable with a separate light source to provide illuminating light. As another alternative, a light-emitting diode or other miniaturizable light source can be disposed at the distal end of the endoscope directly upstream in the light path from the light-refracting device or can be coupled with the latter via a short light conductor.

In particular, the combination of a light conductor, which extends from the proximal to the distal end of the endoscope, and a light-refracting device at the distal end of the endoscope can make possible a small cross-section of the shaft of the endoscope and simultaneously a control of the illuminating light emanating at the distal end of the endoscope, with the aforementioned advantages.

An endoscope as described here can comprise a number of light conductors to transmit illuminating light to the distal end of the endoscope, each with an outlet surface that is disposed at the distal end of the endoscope, and a light-splitting device for controllable switching of illuminating light into one or more of the number of light conductors.

The light-splitting device and the light inlet surfaces of the light conductors are, in particular, disposed at the proximal end of the endoscope where more structural space can be available than in the shaft of the endoscope. One light-refracting device is associated in each case with one, several or all light outlet surfaces of the number of light conductors. In particular, each light outlet surface of a light conductor is directly coupled with a light inlet surface of a light-refracting device, whose light outlet surface simultaneously is the light outlet surface of the endoscope. The combination of a light-splitting device at the proximal end of the endoscope with one or more light-refracting devices at the distal end of the endoscope can, with a small number of light conductors and of light-refracting devices, allow an adjustment of the illuminating direction to the viewing angle.

An endoscope includes a number of light outlet surfaces at the distal end of the endoscope and a number of controllable light-diverting devices for controllable diverting of illuminating light, such that one of the number of controllable light-diverting devices is disposed at each light outlet surface of the endoscope.

Each light-diverting device is, in particular, disposed directly upstream in the light path from the associated light outlet surface of the endoscope, such that the light outlet surface of the endoscope can be identical with the light outlet surface of the light-diverting device. Each light-diverting device can be a light-refracting device, as is described here.

In a method for illuminating an adjustable visual field of an endoscope, illuminating light is provided and a phase interface is formed between two fluids at the distal end of the endoscope for controllable refraction of illuminating light, such that the phase interface is formed depending on the momentarily adjusted visual field of the endoscope.

The endoscope visual field is adjustable, in particular with respect to the viewing angle and/or with respect to the image field angle or solid angle, on the basis of the distal end of the endoscope, within which simultaneously recorded objects are situated. The phase interface between the two fluids is disposed in particular directly upstream in the light path from a light outlet surface of the endoscope. The endoscope can be an endoscope as described here, or can comprise one or more of its properties and features.

In a method as described here, in addition, a control signal can be generated and the control signal can be transmitted to the distal end of the endoscope, such that the forming of the phase interface on the distal end of the endoscope is controlled by means of the control signal.

In a method as described here, several control signals can be generated and transmitted to the distal end of the endoscope in order to control the forming of several phase interfaces at the distal end of the endoscope by one control signal each, to refract illuminating light.

In an endoscope as described here, the light-splitting device can include two non-mixable liquids with different refractive indices and one interface control device for electrical or magnetic modification of at least either the arrangement or the shape of an interface between the non-mixable liquids.

BRIEF DESCRIPTION OF THE DRAWINGS

Embodiments are described in greater detail hereinafter with reference to the appended drawings, which are as follows.

DETAILED DESCRIPTION OF THE INVENTION

Figure 1:
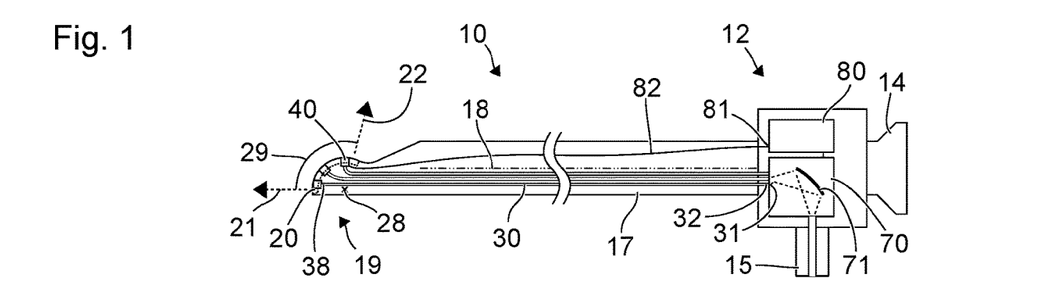
FIG. 1 shows a schematic depiction of an endoscope with adjustable viewing angle.

FIG. 1 shows a schematic depiction of an endoscope 10 with a proximal end 12, a distal end 19 and a rigid shaft 17 that extends from the proximal end 12 to the distal end 19. Alternatively, the shaft 17 is flexible or partly flexible. The cross-section of the shaft 17 or at least the outer contour of the cross-section of the shaft 17 is constant or essentially constant between the proximal end 12 and the distal end 19. In particular, the contour of the cross-section of the shaft 17 is circular or elliptical in shape. In this case the longitudinal axis 18 of the endoscope 10 indicated in FIG. 1 is the axis of symmetry of the mantle surface of the shaft 17 between the proximal end 12 and the distal end 19. In a cylindrical mantle surface of the shaft 17, the longitudinal axis 18 is also the sum of the center points or surface centers of gravity of the cross-sections of the shaft 17 between the proximal end 12 and the distal end 19. In a cylindrical mantle surface of the shaft 17, the longitudinal axis 18 is also the axis of symmetry of the mantle surface.

On the distal end 19, the shape of the shaft 17 departs from the cylindrical symmetry as is depicted by way of example in FIG. 1. In particular, the shaft 17 comprises on the distal end 19 an opening that is closed by a transparent window component 20, indicated in broken lines, with a vaulted surface. In particular, the window component 20 closes the opening with a hermetic sealing. The surface of the window component 20 has, for example, the shape of a portion of a cylindrical mantle, whereby the axis of symmetry of the cylinder is perpendicular to the longitudinal axis 18 of the endoscope 10 and to the plane of projection of FIG. 1. Alternatively, the surface of the transparent window component 20 has the shape of a portion of a spherical surface or of a rotation-symmetrical or non-rotation-symmetrical ellipsoid.

On the distal end 19 of the endoscope 10, optical devices are positioned in the shaft 17 that are not shown in FIG. 1. Said optical devices make it possible to vary the viewing angle of the endoscope between a first extreme viewing angle 21 and a second extreme viewing angle 22. The viewing angle can pivot between the two extreme viewing angles 21, 22 around a pivot axis 28 that is perpendicular to the plane of projection of FIG. 1. The viewing angle in each case is the direction based on the distal end 19 of the endoscope 10 in which an object is situated that appears in the center of an image recorded by means of the endoscope 10.

In the example illustrated in FIG. 1, the first extreme viewing angle 21 is parallel or essentially parallel to the longitudinal axis 18 of the endoscope 10. Situated between the extreme viewing angles 21, 22 is an angle area 29 that comprises approximately 120 degrees in the illustrated example. Within this angle area 29, the viewing angle of the endoscope 10 can be displaced or adjusted, in particular, continually.

At the proximal end 12 the endoscope 10 comprises an eyepiece 14 or a coupling for optical coupling of the endoscope 10 with a video camera. In addition, the endoscope 10 comprises on the proximal end 12 a coupling 15 to couple the endoscope 10 with a light source via a light conductor cable. One or more light conductors 30 lead from the coupling 15 through the shaft 17 to the distal end 19 of the endoscope 10. Distal ends 38 of the light conductors 30 are each coupled with one light-diverting device 40. The light-diverting devices 40 are disposed close to the window component 20, in particular at two opposite edges of the window component 20.

Illuminating light generated by a light source can be transmitted to the distal end 19 of the endoscope 10 by means of a light conductor cable, the coupling 15 and the lightwave conductor or conductors 30. At the distal end 19 of the endoscope 10, the illuminating light exits through the light-diverting devices 40 out of the endoscope 10 in order to illuminate objects that are to be observed. In the process, each light-diverting device 40 diverts or influences the illuminating light with respect to its direction and/or its angle distribution.

The light-diverting devices are, in particular, light-refracting devices, which controllably divert illuminating light by refraction on a shapeable phase interface. Examples of light-refracting devices are described hereinafter with reference to FIGS. 2 through 7.

At the proximal end 12 of the endoscope 10, a light-splitting device 70 is provided for controllable switching of illuminating light, received via the coupling 15, into one or more of the light conductors 30. The illustration shows, by way of example, a curved mirror 71, which can be pivoted. Alternatively, the light-splitting device 70 can include, for example, a light-refracting device with a controllable interface on which the illuminating light is controllably refracted. The light-splitting device 70 is optional. Alternatively, the endoscope can be configured to switch provided illuminating light at all times into all light conductors 30.

In addition, at the proximal end 12 of the endoscope 10, a control device 80 is provided along with a control outlet 81 to provide a control signal. The control outlet 81 is coupled with the light-refracting devices 40 at the distal end 19 of the endoscope 10 via one or more control lines 82. The control device 80 is, in addition, coupled with the light-splitting device 70.

The control device 80 is configured in order to control the light-splitting device 70 and, via the control lines 82, the light-refracting devices 42, depending on a viewings angle 21, 22 adjusted on the endoscope 10. For this purpose, the control device 80 is, in particular, coupled directly or indirectly with a user interface on which a user of the endoscope 10 can adjust the viewing angle of the endoscope 10. Alternatively or in addition, the control device can be configured to control the light-refracting devices 40 and the light-splitting device 70 depending on a focal length adjusted on the endoscope 10 or an adjusted image field angle. The control device 80 is configured to control the light-refracting devices 40 and light-splitting device 70 in such a way that at all times the greatest possible portion of provided illuminating light is radiated into the area that is momentarily observed or optically recorded by means of the endoscope 10 and as little illuminating light as possible is radiated into areas that are momentarily not observed or not optically recorded.

FIGS. 2 through 5 show schematic sectional views of an embodiment of a light-refracting device 40. The illustrated sectional plane is parallel to the plane of projection of FIG. 1. In each case, the curved contour of the distal end 19 of the endoscope 10 is indicated in broken lines.

The light-refracting device 40 includes a first window component 42 on a light inlet side and a second window component 48 on a light outlet side situated opposite. The first window component 42 and second window component 48 each comprise a material that is transparent to the foreseen illuminating light. The first window component 42 and the second window component 48 can each comprise parallel and level surfaces or—contrary to the depictions in FIGS. 2 through 5—one or two curved surfaces. Departing from the depictions in FIGS. 2 through 5, curved surfaces of the window components 42, 48 with a gathering or expanding effect can contribute to beam formation.

The first window component 42 and the second window component 48 are connected with one another by a ring-shaped wall 43. The wall 43, in particular, has the shape of a cylinder with circular, elliptical, square, rectangular or other cross-section. The wall 43 can comprise the same material as the window components 42, 48. Alternatively, the wall 43 can comprise a different material, in particular a non-transparent material.

The wall 43, the first window component 42 and the second window component 48 are joined, in particular cemented or soldered, in order to surround a hollow space in a hermetically insulated manner. In said hollow space sealed off by the window components 42, 48 and the wall 43, two non-mixable fluids are situated, in particular a first liquid 44 and a second liquid 46. The first liquid 44 and the second liquid 46 are not, or essentially not, mixable and constitute a phase interface 45. For example, the first liquid 44 is an aqueous salt solution and the second 46 is an oil, or vice versa. The two liquids 44, 46 are transparent to the foreseen illuminating light and comprise the most diverse refractive indices possible. The two liquids 44, 46 in addition have different properties with respect to their reciprocal effect with electrostatic fields, in particular different electric permittivities or different dielectricity numbers.

Several electrodes 51, 52, 53, 54 to generate electric fields are foreseen on the first window component 42 and on the wall 43. Each individual electrode 51, 52, 53, 54 is coupled with the control device 80 (compare FIG. 1) via a control line 82. Each electrode 51, 52, 53, 54, in particular—as indicated in FIGS. 2 through 5—can be positioned on an external surface of the window component 42 or of the wall 43 or—departing from the illustrations in FIGS. 2 through 5—on an internal surface of the window component 42 or of the wall 43. Contrary to the depictions in FIGS. 2 through 5, in addition one or more transparent electrodes can be provided on the window component 48.

The light-refracting device 40 is coupled with the distal end 38 of the light conductor 30. In particular, the light outlet surface 39 on the distal end 38 of the light conductor 30 is glued, cemented or soldered with the light inlet surface 41 formed by the first window component 42 of the light-refracting device 40, so that the light outlet surface 39 of the light conductor 30 is simultaneously the light inlet surface 41 of the light-refracting device 40. To reduce reflection losses, one or more layers that reduce reflections can be provided on the interface between the light conductor 30 and light-refracting device 40. The light outlet surface 49 of the light-refracting device 40 that is opposite the light inlet surface 41 and is formed by the second window component 48 is, in particular, positioned flush or essentially flush with the external surface of the distal end of the endoscope, which is indicated in FIGS. 2 through 5 in broken lines.

The foreseen propagation path 64 of illuminating light in the light-refracting device 40 is the path from the first window component 42 to the second window component 48.

By means of the light conductor 30, illuminating light can be transmitted from the proximal end 12 to the distal end 19 of the endoscope 10 (compare FIG. 1) and switched there into the light-refracting device 40. Illuminating light is refracted several times because of the different refractive indices of the liquids 44, 46 and window components 42, 48, especially at the phase interface 45 between the liquids 44, 46, before it emerges through the light outlet surface 49 from the light-refractive device 40 and from the endoscope in order to illuminate objects that are to be observed.

By applying different electrical potentials to the electrodes 51, 52, 53, 54, an electric field can be generated in the light-refracting device 40. Because of variable reciprocal effect of the liquids 44, 46 with an electric field, the said field influences the shape of the phase interface 45 between the liquids 44, 46. By varying the electric potential applied via the control lines 82 to the electrodes 51, 52, 53, 54, the spatial shape of the phase interface 45 between the liquids 44, 46 can be varied.

Shown as examples in FIGS. 2 through 5 are four different forms or shapes of the phase interface 45 between the liquids 44, 46, which can be generated by applying different electric potential to the electrodes 51, 52, 53, 54. To generate the illustrated forms of phase interface 45, an arrangement of electrodes differing from the one illustrated can be advantageous.

Figure 2:
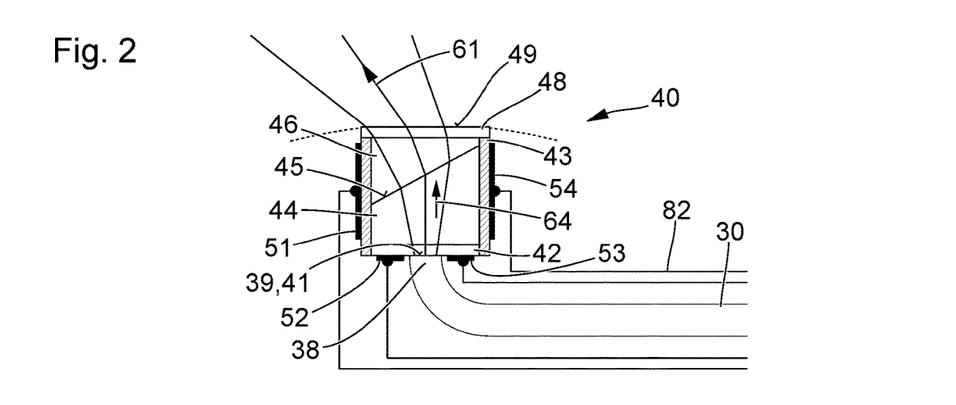
FIG. 2 shows a schematic depiction of a light-refracting device.
Figure 3:
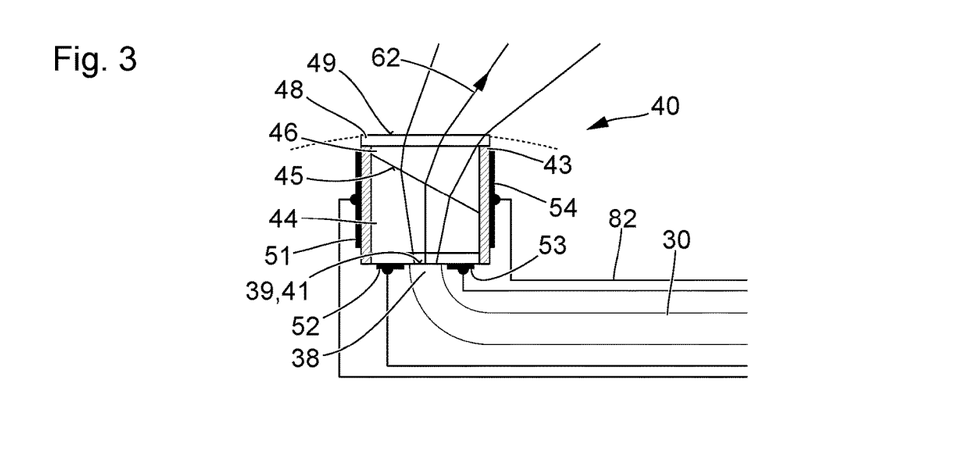
FIG. 3 shows another schematic depiction of a light-refracting device from FIG. 2.

In the examples shown in FIGS. 2 and 3, the phase interface 45 between the liquids 44, 46 is level in each case but tipped in various directions. The different refraction of the illuminating light at the phase interface 45 causes two different illuminating directions 61, 62 in which the illuminating light can be radiated. Owing to a continual variation in the electric potential applied to the electrodes 51, 52, 53, 54, the illuminating direction can be continuously varied, at least between the illuminating directions 61, 62 indicated in FIGS. 2 and 3.

Figure 4:
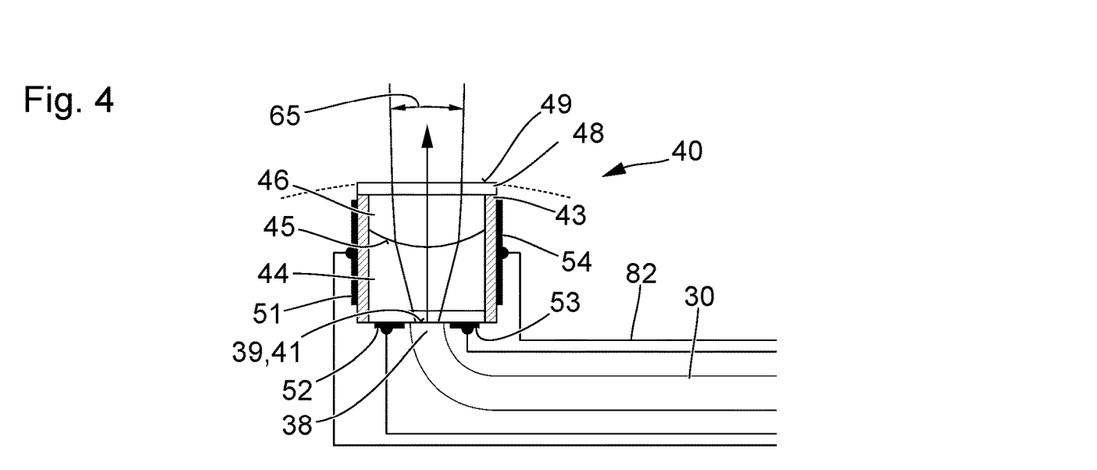
FIG. 4 shows another schematic depiction of the light-refracting device from FIGS. 2 and 3.
Figure 5:
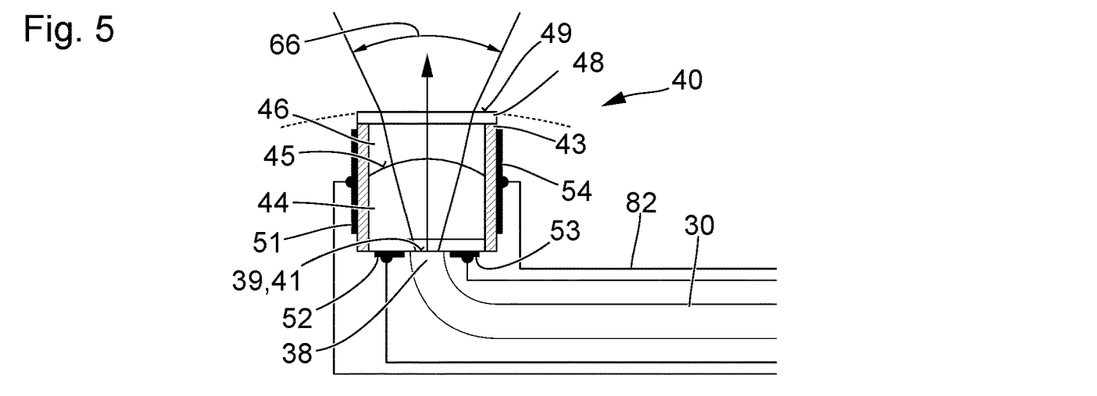
FIG. 5 shows another schematic depiction of the light-refracting device from FIGS. 2 through 4.

In the examples shown in FIGS. 4 and 5, the phase interface 45 between the liquids 44, 46 is vaulted in each case, in opposite directions. The resulting different refraction of the illuminating light causes different opening angles 65, 66 of the light bundle emanating from the endoscope at the light outlet surface 49 of the light-refracting device 40. Because of continuous variation of the electric potential applied to the electrodes 51, 52, 53, 54, the opening angle of the light bundle formed by the light-refracting device 40 can be continuously varied, at least between the opening angles 65, 66 shown in FIGS. 4 and 5.

Whereas in FIGS. 2 through 5 the phase interface 45 between the liquids 44, 46 is shown as only either flat and tipped or symmetrical and curved, it can also be simultaneously tipped and curved by the application of corresponding electric power to the electrodes 51, 52, 53, 54. Instead of electrodes or in addition to them, one or more coils can be provided to generate a magnetic field, contrary to the depictions in FIGS. 2 through 5. In this case, the liquids 44, 46 have different reciprocal actions with a magnetic field, especially different magnetic permeabilities or different magnetic susceptibilities.

Figure 6:
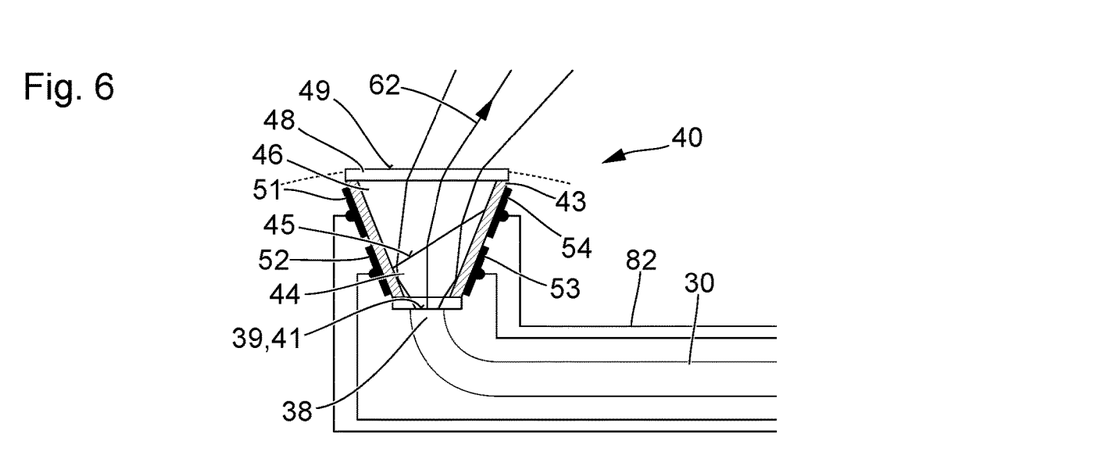
FIG. 6 shows a schematic depiction of an additional light-refracting device.
Figure 7:
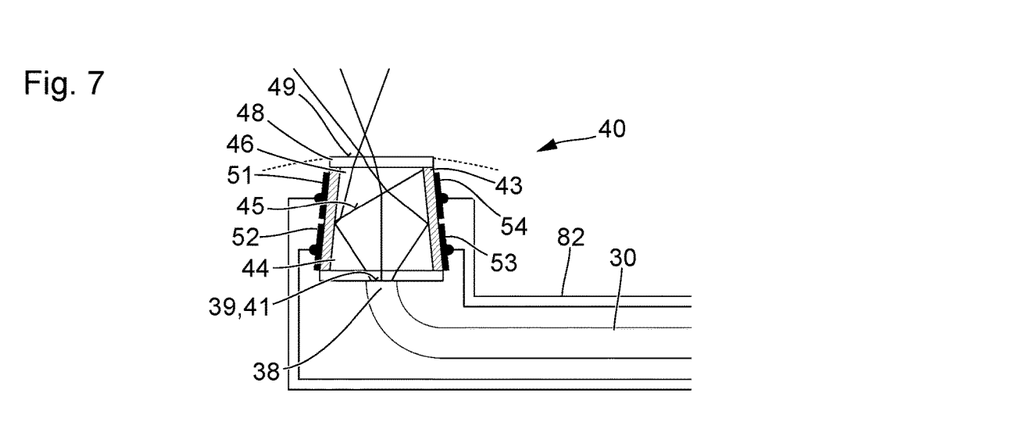
FIG. 7 shows a schematic depiction of an additional light-refracting device.

FIGS. 6 and 7 show schematic depictions of additional light-refracting devices 40, which resemble in some features the light-refracting devices described above with reference to FIGS. 2 through 5. The light-refracting devices 40 shown in FIGS. 6 and 7 differ from the light-refracting device presented above with reference to FIGS. 2 through 5, in particular, in having a different exemplary arrangement of the electrodes 51, 52, 53, 54. In all light-refracting devices shown in FIGS. 2 through 7, fewer or more electrodes than illustrated can be provided. In addition, the electrodes can be arranged otherwise than as indicated in FIGS. 2 through 7.

The light-refracting devices of FIGS. 6 and 7 differ from the light-refracting device shown in FIGS. 2 through 5, in addition, in a non-cylindrical shape of the wall 43 between the first window component 42 and the second window component 48. In the light-refracting devices 40 shown in FIGS. 6 and 7, the wall 43 has in each case the shape of a portion of a mantle surface of a pyramid with square, rectangular or polygonal base surface or of a cone with circular, elliptical or other base surface. In addition, non-cut portions of the wall 43 in FIGS. 6 and 7 can have a different shape, for example being flat and parallel to one another and to the sectional planes of FIGS. 6 and 7.

The cross-section of the light-refracting device 40, which varies in the foreseen propagation path of illuminating light, influences the divergence or angle distribution of the illuminating light emanating from the endoscope at the light outlet surface 49 of the light-refracting device 40. In particular, a cross-section that widens in the propagation path of the illuminating light, as is shown in FIG. 6, can reduce the divergence of the emanating light. A width of the cross-section of the light-refracting device 40 that decreases in the foreseen propagation path of illuminating light, as is indicated in FIG. 7, can increase the divergence of the illuminating light.

Figure 8:
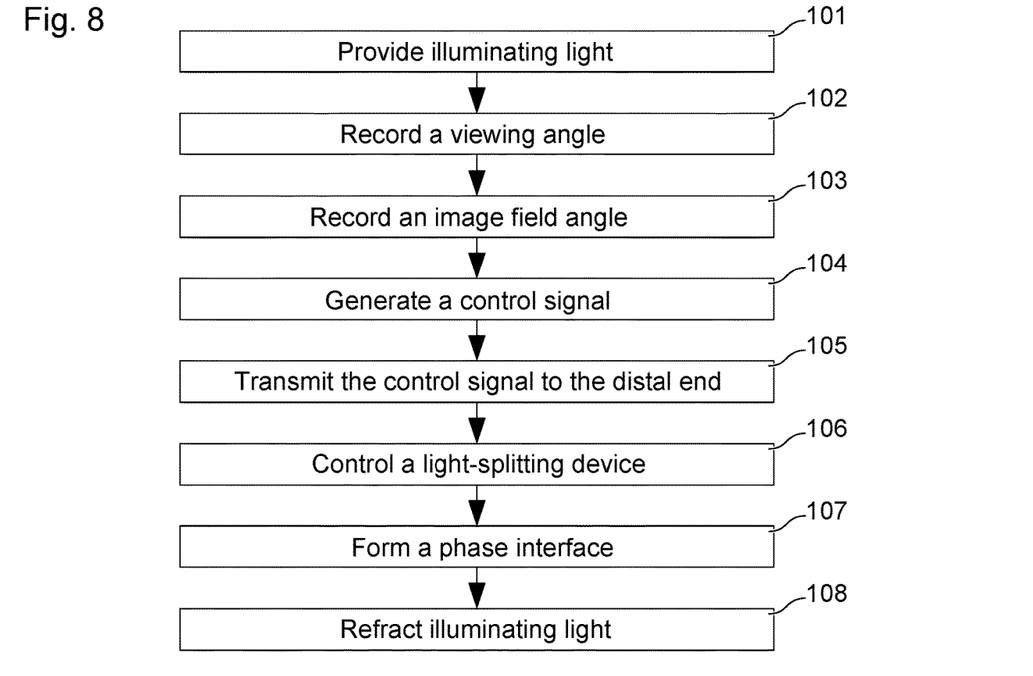
FIG. 8 shows a schematic flow diagram of a method for illuminating.

FIG. 8 shows a schematic flow diagram for a method for illuminating an adjustable visual field of an endoscope. Although the method can also be performed with an endoscope that has different features from those described above with reference to FIGS. 1 through 7, reference numbers from FIGS. 1 through 7 are used by way of example in the following description in order to facilitate understanding. In a first step 101, illuminating light is provided. The illuminating light can be generated at the distal end 19 or proximal end 12 of the endoscope or in a separate light source device and can be transmitted to the endoscope 10 by means of a light conductor cable. If necessary, the illuminating light is transmitted from the proximal end 12 to the distal end 19 of the endoscope by means of a light conductor 30.

In a second step 102, a momentary viewing angle 21, 22 of the endoscope 10 adjusted by the user is recorded. In a third step 103, an image field angle momentarily adjusted by a user at the user interface of the endoscope 10 is recorded. In a fourth step 104, a control signal is generated, in particular by a control device 80, depending on the recorded viewing angle and the recorded image field angle. The control signal is, for example, an electric tension or current signal. In a fifth step 105, the control signal generated in the fourth step 104 is transmitted to the distal end 19 of the endoscope.

In an optional sixth step 106, a light-splitting device 70 is controlled, depending on the viewing angle recorded in the second step 102 and on the image field angle recorded in the third step, in order to switch illuminating light provided in the first step 101 into one or more light conductors 30 of a number of light conductors 30.

In a seventh step 107, controlled by the control signal generated in the fourth step 104 and transmitted in the fifth step 105 to the distal end 19 of the endoscope 10, a phase interface is formed between two fluids with different optical features, in particular tipped and/or curved. In an eighth step 108, the illuminating light provided in the first step 101 and if necessary transmitted to the distal end 19 of the endoscope 10 is refracted at the phase interface formed in the seventh step 107. The refraction of the illuminating light and thus its direction and angle distribution are dependent on the form or shape of the phase interface 45 generated in the seventh step 107.

What is claimed is:

1. An endoscope, comprising:
   a proximal end, a distal end, and a shaft that extends from the proximal end to the distal end;
   an optical device providing an adjustable viewing angle, the adjustable viewing angle being adjustable about a pivot axis between a first viewing angle and a second viewing angle;
   a light outlet surface at the distal end of the endoscope through which illuminating light is projected out of the endoscope;
   a controllable light refracting device adjusting refraction of the illuminating light by means of a shapeable phase interface between two fluids, the controllable light-refracting device being positioned at the distal end of the endoscope such that a light outlet surface of the controllable light-refracting device forms at least a part of the light outlet surface at the distal end of the endoscope;
   the controllable light-refracting device being configured to adjust at least one of a direction of the illuminating light or an opening angle of an area that is to be illuminated by the illuminating light dependent on the adjustable viewing angle of the endoscope; and
   a control device generating a control signal to control the controllable light-refracting device at least depending on one of the adjustable viewing angle or a focal length adjusted on the endoscope.

2. The endoscope according to claim 1, wherein
   the endoscope comprises a number of light outlet surfaces at the distal end, and
   a light-refracting device is positioned at each of the number of light outlet surfaces.

3. The endoscope according to claim 1, wherein the light-refracting device comprises a cross-section of which at least either a surface or a width increases in a foreseen propagation path of illuminating light.

4. The endoscope according to claim 1, wherein the light-refracting device comprises a cross-section of which at least either a surface or a width decreases in a foreseen propagation path of illuminating light.

5. The endoscope according to claim 1, further comprising:
   a field-generating device to generate an electric or magnetic field to form the phase interface.

6. The endoscope according to claim 1, further comprising several light-refracting devices positioned at the distal end of the endoscope, wherein the control device is configured to generate one signal for each of the several light-refracting devices.

7. The endoscope according to claim 1, further comprising:
   a light conductor to transmit illuminating light to the distal end of the endoscope, the light conductor having a light outlet surface disposed at the distal end of the endoscope,
   wherein the light-refracting device is disposed between the light outlet surface of the light conductor and the light outlet surface of the endoscope.

8. The endoscope according to claim 7, further comprising:
   a number of light conductors to transmit illuminating light to the distal end of the endoscope, each light conductor having one light outlet surface that is disposed at the distal end of the endoscope, and
   a light-splitting device for controllable switching of illuminating light into one or more of the number of light conductors.

9. The endoscope according to claim 1, wherein the control device controls the light-refracting device so that illuminating light is directed in a direction corresponding to a viewing direction of the endoscope.

10. The endoscope according to claim 1, wherein the control device controls the light-refracting device so that the opening angle that is to be illuminated corresponds to a visual field angle of the endoscope.

11. An endoscope, comprising:
- a proximal end, a distal end, and a shaft that extends from the proximal end to the distal end;
- a light outlet surface at the distal end of the endoscope;
- a controllable light-refracting device adjusting refraction of illuminating light by means of a shapeable phase interface between two fluids, the controllable light-refracting device being positioned at the distal end of the endoscope such that a light outlet surface of the controllable light-refracting device forms at least a part of the light outlet surface at the distal end of the endoscope;
- the controllable light-refracting device having an enclosure formed by a light outlet window, light inlet window, and a wall connecting both windows, the wall and the light inlet window each having at least one electrode or coil to adjust the shapeable phase interface and change at least one of a direction of illuminating light projecting out of the endoscope or an opening angle of an area that is to be illuminated by illuminating light projecting out of the endoscope; and
- a control device generating a control signal to control the controllable light-refracting device at least depending on an adjustment of at least either a viewing angle or an image field angle of the endoscope.

\* \* \* \* \*